(12) United States Patent
McCole

(10) Patent No.: US 11,150,237 B2
(45) Date of Patent: Oct. 19, 2021

(54) **PATIENT-SPECIFIC BIOMARKERS OF *ESCHERICHIA COLI* INVASION IN INFLAMMATORY BOWEL DISEASE**

(71) Applicant: The Regents of the University of California, Oakland, CA (US)

(72) Inventor: Declan McCole, Yorba Linda, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/371,935

(22) Filed: Apr. 1, 2019

(65) Prior Publication Data

US 2019/0302103 A1 Oct. 3, 2019

Related U.S. Application Data

(60) Provisional application No. 62/650,823, filed on Mar. 30, 2018.

(51) Int. Cl.
*G01N 33/53* (2006.01)
*G01N 33/50* (2006.01)
*A61K 38/17* (2006.01)
*A61K 9/00* (2006.01)
*C07K 16/18* (2006.01)
*A61P 1/00* (2006.01)

(52) U.S. Cl.
CPC ......... *G01N 33/5091* (2013.01); *A61K 38/17* (2013.01); *A61K 9/0053* (2013.01); *A61P 1/00* (2018.01); *C07K 16/18* (2013.01); *G01N 2800/065* (2013.01)

(58) Field of Classification Search
None
See application file for complete search history.

(56) References Cited

U.S. PATENT DOCUMENTS

2016/0271204 A1 9/2016 Markel

FOREIGN PATENT DOCUMENTS

WO 2018/015468 A1 1/2018

OTHER PUBLICATIONS

Barnich et al., CEACAM6 acts as a receptor for adherent-invasive E. coli, supporting ileal mucosa colonization in Crohn disease, The Journal of Clinical Investigation, 117(6), Jun. 2007, pp. 1566-1574.
McCole; Regulation of epithelial barrier function by the inflammatory bowel disease candidate gene, PTPN2; Ann N Y Acad Sci.; 1257; Jan. 16, 2018; pp. 108-114.
Shawki et al., Mechanisms of Intestinal Epithelial Barrier Dysfunction by Adherent-Invasive *Escherichia coli*, Cellular and Molecular Gastroenterology and Hepatology, 3(1), 2017, pp. 41-50.

*Primary Examiner* — Christine J Saoud
*Assistant Examiner* — Jon M Lockard
(74) *Attorney, Agent, or Firm* — Kilpatrick Townsend & Stockton LLP

(57) ABSTRACT

The present invention provides methods of detecting increased carcinoembryonic antigen-related cell adhesion molecule (CEACAM) protein expression in a biological sample from a patient with a loss of function mutation in a protein tyrosine phosphatase non-receptor type 2 (PTPN2) gene. The invention also provides methods of treating or preventing inflammatory bowel disease (IBD) in a patient with a loss of function mutation in a protein tyrosine phosphatase non-receptor type 2 (PTPN2) gene.

5 Claims, 3 Drawing Sheets

PATIENT-SPECIFIC BIOMARKERS OF *ESCHERICHIA COLI* INVASION IN INFLAMMATORY BOWEL DISEASE

CROSS-REFERENCE TO RELATED APPLICATIONS

This application claims priority benefit of U.S. provisional application No. 62/650,823, filed Mar. 30, 2018, which is incorporated by reference herein for all purposes.

BACKGROUND OF THE INVENTION

Crohn's Disease and Ulcerative Colitis (collectively referred to as Inflammatory Bowel Disease or IBD) are chronic, inflammatory diseases of the gastrointestinal tract. These diseases are characterized by abdominal pain, diarrhea, a variable group of 'extra-intestinal' manifestations (such as arthritis, uveitis, skin changes) and the accumulation of inflammatory cells within the small intestine and colon.

IBD is a chronic, lifelong disease, and is often grouped with other so-called "autoimmune" disorders (e.g. rheumatoid arthritis, type I diabetes mellitus, multiple sclerosis, etc). There is a clear trend towards the increasing incidence of IBD in the US and Europe, particularly Crohn's Disease.

In spite of considerable research into therapies for these disorders, IBD remains difficult to diagnose and treat effectively. Accordingly, there is a need in the art for improved methods for detecting and treating such inflammatory bowel diseases. The present invention addresses these and other needs.

BRIEF SUMMARY OF THE INVENTION

The present invention provides methods of detecting increased carcinoembryonic antigen-related cell adhesion molecule (CEACAM) protein expression in a biological sample from a patient with a loss of function mutation in a protein tyrosine phosphatase non-receptor type 2 (PTPN2) gene. The methods comprise contacting the biological sample with a binding agent that specifically binds the CEACAM protein and comparing the level of the CEACAM protein present in the biological sample to a control level, thereby determining the presence or absence of increased expression in the biological sample.

The invention also provides methods of treating or preventing inflammatory bowel disease (IBD), celiac diseases, or colorectal cancer in a patient with a loss of function mutation in a protein tyrosine phosphatase non-receptor type 2 (PTPN2) gene. These methods comprise administering to the patient a pharmaceutical composition comprising a therapeutically effective dose of an inhibitory agent capable of inhibiting binding of a CEACAM protein to an adherent-invasive *Escherichia coli* (AIEC).

DETAILED DESCRIPTION OF THE INVENTION

Figure 1:
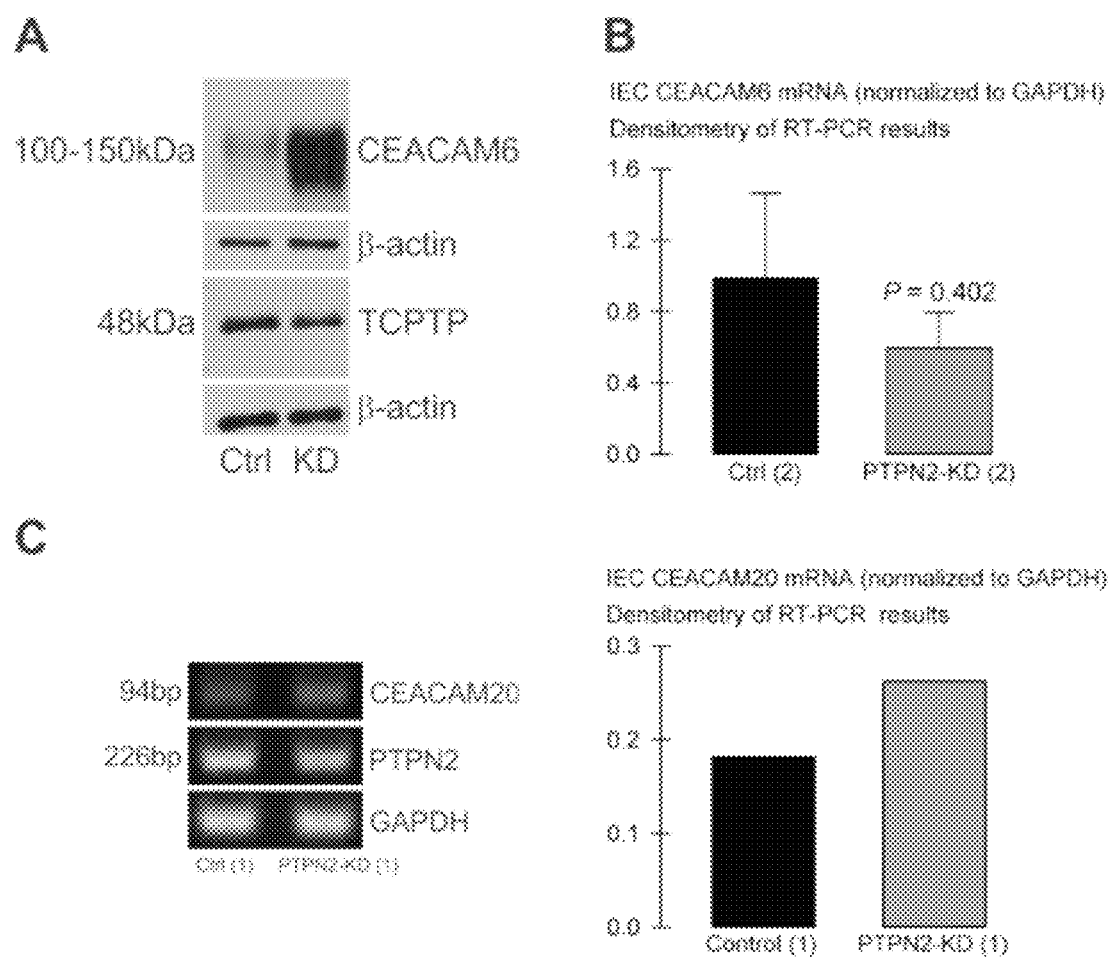
FIG. 1. Protein expression of human CEACAM6 in human IECs. Panel A provides results using control and PTPN2-KD cell lysates that confirm reduced protein expression of TCPTP (PTPN2) in PTPN2-deficient cells and show increased CEACAM6 protein in PTPN2-deficient cells cf. control cells. Panel B provides results of RT-PCR of CEACAM6 mRNA and corresponding densitometry from control and PTPN2-KD IECs (n=3). Panel C shows results of RT-PCR of CEACAM20 mRNA from control and PTPN2-KD IEC lysates (n=1).

Alterations in the intestinal microbiome are an emerging environmental factor in the pathogenesis of inflammatory bowel disease (IBD). Dysfunction of the IBD candidate gene, protein tyrosine phosphatase non-receptor type 2 (PTPN2), which encodes the T-cell protein tyrosine phosphatase (TCPTP) protein (also referred to as tyrosine-protein phosphatase non-receptor type 2 PTPN2 protein), contributes to alterations in the intestinal microbiome and the onset of chronic intestinal inflammation in vivo. Expansion of intestinal pathobionts, such as adherent-invasive *Escherichia coli* (AIEC), can increase susceptibility to colitis in a genetically-susceptible host, and is implicated in IBD, celiac disease and colorectal cancer. The AIEC binding protein, carcinoembryonic antigen-related cell adhesion molecule 6 (CEACAM6), is increased in IBD, and promotes AIEC pathogenesis. The present invention is based, at least in part, on the discovery that loss of TCPTP function promotes pathobiont expansion by altering expression of CEACAM6. Thus, CEACAM6 can be used as a biomarker of susceptibility to AIEC colonization in patients with loss-of-function mutations in the PTPN2 gene for IBD, celiac disease and colorectal cancer. In addition, blocking AIEC binding to CEACAMs proteins (e.g., CEACAM6) is effective in patients with loss-of-function mutations in the PTPN2 gene in these diseases.

A "loss-of function mutation" in a TCPTP protein refers to a mutation in a TCPTP protein (Uniprotein accession number P17706, encoded by PTPN2, which is cytogenetically mapped to human chromosome 18p11.21) that decreases the level of TCPTP protein or function of TCPTP protein (see, e.g., Spalinger et al., *Cell Reports* 22:1835-1848, 2018, Sharp et al., *Front. Cell Infect. Microbiol.* 5:95, 2015 and references cited therein regarding PTPN2 variants associated with IBD) compared to levels of function in a normal healthy subject that does not have chronic inflammatory disease or cancer.

Diagnostic Methods

A number of binding agents can be used to detect CEACAM proteins (e.g., CEACAM6, which is also referred to as CD66c) in a biological sample or can be assessed in the methods of the invention for the ability to inhibit binding of AIEC to intestinal epithelial cells (LECs). The detection and/or quantification of CECAM proteins can be accomplished using any of a number of well recognized binding assays. For example, the presence of CEACAM protein may be detected using standard electrophoretic and immunodiagnostic techniques, including immunoassays. Such assays include in particular Western blots, agglutination tests, enzyme-linked immunosorbent assays (ELISA), avidin/biotin-type assays, radioimmunoassays, immunoelectrophoreses, immunoprecipitations, and the like. The reactions generally include visualization of markers such as fluorescent, chemiluminescent or radioactive molecules or enzymatic markers.

A binding agent used in the assays of the invention can be any molecule or complex of molecules capable of specifically binding to a target CEACAM protein. A binding agent of the invention includes any molecule, e.g., proteins, small organic molecule, carbohydrates (including polysaccharides), oligonucleotides, polynucleotides, lipids, and the like. In some embodiments, the binding agent is an antibody or fragment thereof. Such antibodies are well-known in the art and include commercially available antibodies, e.g., CEACAM6 antibodies such as those from Aviva Systems Biology, Abnova, R&D Systems, and Thermo Fisher Scientific, among other. Specific binding in the context of the present invention refers to a binding reaction which is determinative of the presence of a target protein in the presence of a heterogeneous population of proteins and other biological molecules. Thus, under designated assay conditions, the specified binding agents bind preferentially to a particular protein or isoform of the particular protein and do not bind in a significant amount to other proteins or other isoforms present in the sample.

When the binding agents are antibodies, they may be monoclonal or polyclonal antibodies. The term antibody as used herein refers to immunoglobulin molecules and immunologically active portions of immunoglobulin (Ig) molecules. Such antibodies include, but are not limited to, polyclonal, monoclonal, mono-specific polyclonal antibodies, antibody mimics, chimeric, single chain, Fab, Fab' and F(ab')$_2$ fragments, Fv, and an Fab expression library.

The binding agents of the invention may be labeled and are then referred to as "labeled binding agents". A label is a molecule that can be directly (i.e., a primary label) or indirectly (i.e., a secondary label) detected. The label can be visualized and/or measured or otherwise identified so that its presence or absence can be detected by means of a detectable signal. Examples include fluorescent molecules, enzymes (e.g., horseradish peroxidase), particles (e.g., magnetic particles), chromophores, phosphors, chemiluminescers, specific binding molecules (e.g., biotin and streptavidin, digoxin and antidigoxin), and the like.

The CEACAM proteins are detected in a biological sample taken from the patient. A biological sample may be an ileal biopsy or a preparation of IECs isolated from an ileal biopsy. The biological sample may also be a sample of a biological fluid, such as blood or serum, or alternatively a stool sample.

The binding assays of the invention will typically involve comparison of the level of expression of the CEACAM protein in the biological sample with the level of expression of the protein in a control level of expression. The control may be derived from a biological sample from a healthy subject not suffering from IBD, celiac disease, or colorectal cancer or a biological sample from a patient previously determined to have IBD, celiac disease, or colorectal cancer.

Therapeutic Methods

The present invention also provides therapeutic methods for the prevention or treatment of IBD, celiac disease, or colorectal cancer. Any agent that specifically inhibits the interaction between the CEACAM protein (e.g., CEACAM6) and AIEC can be used in the methods of the invention. The inhibitory agent may be, for example, an anti-CEACAM antibody which specifically recognizes the protein and blocks the binding of the protein to an AIEC strain. The inhibitory agent may also be a fragment of the CEACAM protein or a synthetic protein mimicking the CEACAM protein. The inhibitor can also be a peptide that binds directly to CEACAM6, such as a CEACAM8 peptide and CART (cocaine and amphetamine regulated transcript) peptide. Suitable inhibitory agents may also include carbohydrates (e.g., D-mannose) and other agents described, for example, in U.S. Pat. No. 9,176,131 and WO 01/013937, which are incorporated herein by reference.

One of skill will recognize that a variety of antibodies can be used in the therapeutic methods of the invention. These include natural or genetically modified forms such as humanized, human, single-chain, chimeric, bispecific, synthetic, antibody fragments, recombinant, hybrid, mutated, grafted, and in vitro generated antibodies.

The inhibitory agents are prepared in pharmaceutical compositions for administration according to methods well known to those of skill in the art. The composition will commonly comprise an inhibitory agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate water solubility and/or physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

The pharmaceutical compositions can be administered in a variety of unit dosage forms depending upon the method of administration. For example, unit dosage forms suitable for oral administration include, but are not limited to, powder, tablets, pills, capsules and lozenges. In some embodiments, the agents of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Further in accordance with the present invention, there are provided pharmaceutical composition for administering to human or veterinary patients, the compositions are typically used for oral administration, but other routes may also be used, e.g., rectal, intravenous, intraarterial, intradermal, subcutaneous, intramuscular, intrathecal, sublinginual, bucal, intranasal, trans-mucosal, trans-dermal, and topical.

The compositions containing inhibitory agents of the invention can be administered for therapeutic or prophylactic treatments. In therapeutic applications, compositions are administered to a patient suffering from IBD (e.g., Crohn's disease), celiac disease, or colorectal cancer in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. An amount of an inhibitor that is capable of preventing or slowing the development of a disease in a patient is referred to as a "prophylactically effective dose." The particular dose required for a prophylactic treatment will depend upon the medical condition and history of the patient, the particular disease being prevented, as well as other factors such as age, weight, gender, administration route, efficiency, etc. Such prophylactic treatments may be used, e.g., in a patient who has previously had a disease to prevent a recurrence, or in a patient who is suspected of having a significant likelihood of developing the disease.

Examples

Approximately $4 \times 10^{13}$ bacteria exist in the gastrointestinal tract with more than 35,000 bacterial species that play a major role in maintaining intestinal homeostasis.[24-26] Alterations in the intestinal microbiome are an important factor in the pathogenesis of IBD.[27] Expansion of intestinal pathobionts, such as AIEC, can induce a pro-inflammatory cytokine (IFN-γ, TNF-α, IL-13) response; increase susceptibility to colitis in a genetically-susceptible host; disrupt expression and distribution of TJ proteins; and AIEC itself is strongly implicated in the pathogenesis of IBD.[3; 4; 28-32] Moreover, intestinal levels of CEACAM6, to which AIEC binds, are increased in IBD, possibly mediating AIEC pathogenesis.[7]

Conversely, reductions in the abundance of commensal bacteria occur in IBD patients and may also contribute to IBD pathogenesis.[5] Segmented-filamentous bacteria (SFB) are spore-forming gram positive anaerobes. They are part of the resident microbiota in a variety of species, including humans and are highly expressed during early infancy, consistent with their role in maturation of the immune system.[33; 34] In addition, SFB have been shown to prevent colonization of E. coli in rabbits;[8] however, the mechanism is unknown. SFB are associated with the epithelium and preferentially attach to "microfold" or M-cells and Peyer's patches—both of which are sites of inducible CEACAM6 expression.[35; 36] This may suggest a mechanistic connection between SFB and CEACAM levels in protecting against AIEC infection.

Methods:

Mouse AIEC (mAIEC) isolated from distal colon of Ptpn2-deficient mice was used to infect HT-29 intestinal epithelial cells (IEC) for 3 hrs. Anti-CEACAM6 blocking antibody was used to interrupt mAIEC binding (1 hr pre-treatment at 1:100). Caco-2 cells stably expressing scrambled shRNA and shRNA against PTPN2 were used for bacterial adherence-invasion (3 hr infection), RNA-isolation, and protein isolation. RNA-Seq libraries were generated by depleting ribosomal RNA from total RNA and sequenced on the Illumina NextSeq2000 platform. Analysis was performed with systemPipeR. Reads were aligned to the human genome (hg38) using Tophat and differentially expressed genes (DEGs) were identified using EdgeR. DEGs were defined as those with a fold change$\geq$2 and FDR-adjusted P value$\leq$0.05. CEACAM expression in isolated mouse IEC was determined by RT-PCR and Western blot.

CEACAM proteins have been implicated in AIEC adherence and invasion.[4] Notably, intestinal levels of CEACAM1, CEACAM6, and CEACAM20 are increased in IBD.[7; 41; 42] We identified a significant upregulation of CEACAM6 protein in human PTPN2-KD IECs cf. control cells (FIG. 1, Panel A). This effect may be post-transcriptional as we saw no change in CEACAM6 mRNA (FIG. 1, Panel B). However, CEACAM20 mRNA expression appears higher in PTPN2-KD IECs cf. control cells (FIG. 1, Panel C).

Figure 2:
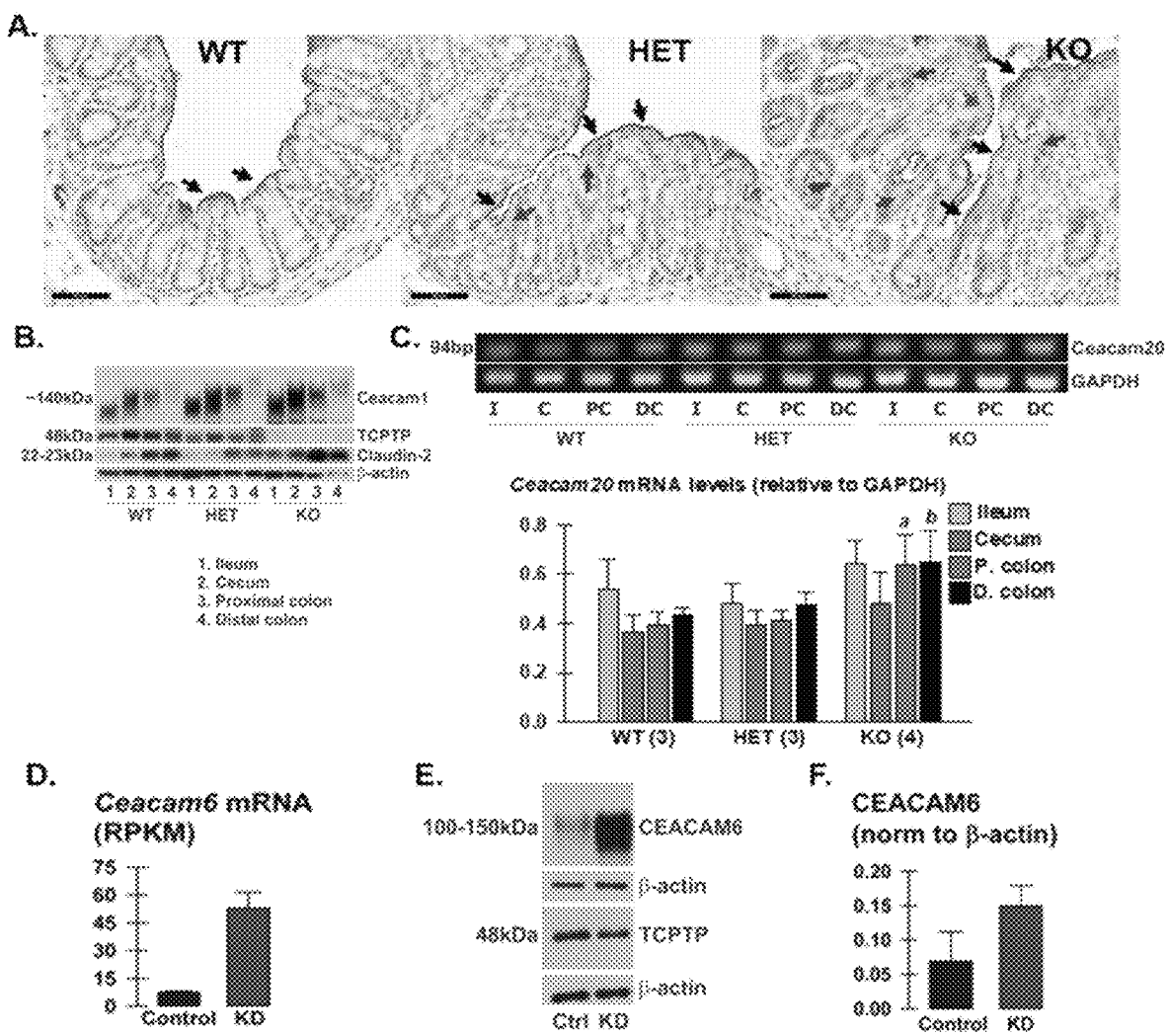
FIG. 2. PTPN2 restricts intestinal epithelial cell (IEC) expression of human and murine AIEC-binding CEACAMs. Panel A shows CEACAM1 staining (IHC) in Ptpn2 WT, Het and KO mouse cecum (n=2). Apical membrane (black arrows) and cytoplasmic staining are indicated (bar=50 µm). Panel B provides results of Western blot of IECs from different gut regions, which showed elevated CEACAM1 and reduced TCPTP (PTPN2) protein in Ptpn2 Het and KO mice. Panel C provides results illustrating that Ceacam20 mRNA was increased (a,b, $p<0.05$) in proximal and distal colon IEC lysates from Ptpn2-KO mice vs. WT ('n' in parentheses). Panel D provides RNAseq results showing elevated Ceacam6 mRNA in PTPN2-KD HT-29 human IECs vs. Con-shRNA (FDR-corrected $p<0.001$, n=2). Panel E provides Western blot results and Panel F provides densitometry results showing increased CEACACM6 in PTPN2-deficient (KD) cells cf. controls ($p=0.02$, n=4).

Because CEACAM6 is not expressed in mice, we next screened for CEACAM1 expression. CEACAM1 protein levels in the large intestine (Cecum) were observed by immunohistochemical staining of fixed tissue in Ptpn2 heterozygous (Het), and knock-out (KO) mice compared with wild-type (WT) (FIG. 2, Panel A). Increased CEACAM1 protein was also found by Western blotting of intestinal epithelial cells isolated from ileum, cecum, proximal and distal colon of Ptpn2 heterozygous (Het), and knock-out (KO) mice compared with wild-type (WT) (FIG. 2, Panel B). Ceacam20 mRNA expression was significantly increased in proximal and distal colon IECs of Ptpn2-KO mice compared with WT mice (FIG. 2, Panel C). Using control or PTPN2-knockdown (KD) human intestinal epithelial cell lines, we showed that CEACAM6 mRNA (FIG. 2, Panel D) and protein (FIG. 2, Panels E and F) is increased in PTPN2-deficient (PTPN2-KD) epithelial cells.

CEACAM20 protein level is evaluated to determine if it is altered in Ptpn2-deficient murine and human IECs and other CEACAMs (10 and 18) are evaluated to determine if a linear relationship exists between CEACAM mRNA and protein expression, or if post-translational processing is more significant in modulating CEACAM levels than transcriptional regulation. In sum, PTPN2 loss increases the ability of mAIEC to invade IECs through increased expression of a subset of CEACAM proteins.

Figure 3:
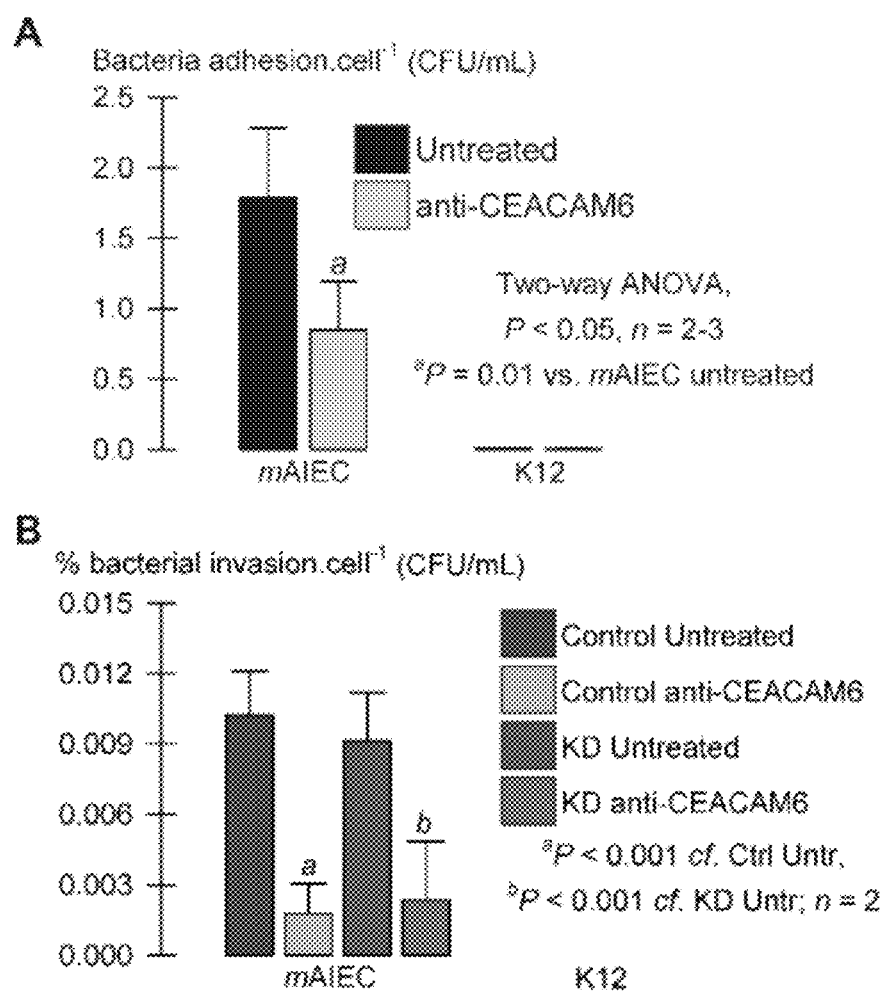
FIG. 3. Blocking adherence and invasion of mAIEC to IECs. HT29 cells pre-treated with 1:100 anti-human CEACAM6 antibody for 1 hour prior to infection with mAIEC. Panel A provides results showing that mAIEC adherence is partially blocked in cells pre-treated with CEACAM6 antibody (n=2). Panel B provides results showing that blocking CEACAM6 prevents invasion of mAIEC in both control and PTPN2-KD IECs (n=2).

Having identified that increased CEACAM expression is associated with increased mAIEC abundance and invasion, we next confirmed a functional role for CEACAM6 in mediating AIEC adherence and invasion of IECs.[7] A CEACAM6 blocking antibody significantly reduced mAIEC adherence (p<0.05; FIG. 3, Panel A), and invasion to both control and PTPN2-KD IECs compared with untreated IECs (P<0.05; n=2; FIG. 3, Panel B). This further indicates CEACAM6 mediation of AIEC pathogenesis.

Summary of Results:

In PTPN2-KD Caco-2 cells, mAIEC showed significantly increased invasion (40±0.4% above control cells; n=6, P<0.001), despite reduced adherence (39±14% above control cells; n=6, P=0.009). PTPN2-KD cells showed a 2.8-fold increase (n=2, P<0.001) in mRNA and 3.3-fold increase (n=4, P<0.001) in protein expression of CEACAM6 vs. control cells. Blocking CEACAM6 reduced adherence of mAIEC (by 47±0.4% of untreated cells; n=2-3, P<0.05) compared with untreated HT-29 IEC. While CEACAM6 is not expressed in mice, KO mouse IEC showed increased CEACAM1 protein in the proximal colon (1.5-fold increase) and distal colon (2.1-fold increase) vs. WT mice, and increased CEACAM20 mRNA in the proximal colon (1.6- fold increase; n=3-4, P<0.05) and distal colon (1.5-fold increase; n=3-4, P<0.05) vs. WT mice.

Conclusion:

PTPN2 loss increases expression of epithelial binding proteins that elevate host susceptibility to AIEC invasion. This identifies a mechanism by which IBD-associated PTPN2 loss of function mutations contribute to IBD.

These data indicate:
Loss of PTPN2 activity promotes increased expression of CEACAM proteins (CEACAM6 in human intestinal epithelial cells; CEACAM 1 and 20 in mouse intestine) that are biomarkers for susceptibility to AIEC invasion.
We confirmed by anti-CEACAM6 antibody blocking studies that PTPN2 loss makes intestinal epithelial cells more susceptible to AIEC invasion.
CEACAM6 is a biomarker of susceptibility to AIEC colonization in patients with loss-of-function mutations in the IBD susceptibility PTPN2 gene (Diagnostic).
Strategies to block AIEC binding to CEACAMs and CEACAM6 in humans, is effective in patients with loss-of-function mutations in the PTPN2 gene (Therapeutic).

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

1. Jostins L, et al. Host-microbe interactions have shaped the genetic architecture of inflammatory bowel disease. Nature. 2012; 491:119-124.
2. Franke A, et al. Replication of signals from recent studies of Crohn's disease identifies previously unknown disease loci for ulcerative colitis. Nat Genet. 2008; 40:713-715.
3. Martinez-Medina M, Garcia-Gil L J. *Escherichia coli* in chronic inflammatory bowel diseases: An update on adherent invasive *Escherichia coli* pathogenicity. World J Gastrointest Pathophysiol. 2014; 5:213-227.
4. Shawki A, McCole D F. Mechanisms of Intestinal Epithelial Barrier Dysfunction by Adherent-Invasive *Escherichia coli*. Cellular and Molecular Gastroenterology and Hepatology. 2016; 3:41-50.
5. Sartor R B, Mazmanian S K. Intestinal Microbes in Inflammatory Bowel Diseases. Am J Gastroenterol Suppl. 2012; 1:15-21.
6. You-Ten K E, et al. Impaired bone marrow microenvironment and immune function in T cell protein tyrosine phosphatase-deficient mice. J Exp Med. 1997; 186:683-693.
7. Barnich N, et al. CEACAM6 acts as a receptor for adherent-invasive *E. coli*, supporting ileal mucosa colonization in Crohn disease. J Clin Invest. 2007; 117:1566-1574.
8. Heczko U, et al. Segmented filamentous bacteria prevent colonization of enteropathogenic *Escherichia coli* O103 in rabbits. J Infect Dis. 2000; 181:1027-1033.
9. Atarashi K, et al. Th17 Cell Induction by Adhesion of Microbes to Intestinal Epithelial Cells. Cell. 2015; 163:367-380.
10. Khor B, et al. Genetics and pathogenesis of inflammatory bowel disease. Nature. 2011; 474:307-317.
11. ten Hoeve J, et al. Identification of a nuclear Stat1 protein tyrosine phosphatase. Mol Cell Biol. 2002; 22:5662-5668.
12. Yamamoto T, et al. The nuclear isoform of protein-tyrosine phosphatase TC-PTP regulates interleukin-6-mediated signaling pathway through STAT3 dephosphorylation. Biochem Biophys Res Commun. 2002; 297:811-817.
13. Heinonen K M, et al. T-cell protein tyrosine phosphatase deletion results in progressive systemic inflammatory disease. Blood. 2004; 103:3457-3464.
14. Scharl M, et al. Protection of epithelial barrier function by the Crohn's disease associated gene protein tyrosine phosphatase n2. Gastroenterology. 2009; 137:2030-2040.
15. Matter K, Balda M S. Signalling to and from tight junctions. Nat Rev Mol Cell Biol. 2003; 4:225-236.
16. Clayburgh D R, et al. A porous defense: the leaky epithelial barrier in intestinal disease. Lab Invest. 2004; 84:282-291.
17. Furuse M, Tsukita S. Claudins in occluding junctions of humans and flies. Trends Cell Biol. 2006; 16:181-188.
18. Garcia-Hernandez V, et al. Intestinal epithelial claudins: expression and regulation in homeostasis and inflammation. Ann N Y Acad Sci. 2017; 1397:66-79.
19. Weber C R, et al. Claudin-1 and claudin-2 expression is elevated in inflammatory bowel disease and may contribute to early neoplastic transformation. Lab Invest. 2008; 88:1110-1120.
20. Weber C R, et al. Epithelial myosin light chain kinase activation induces mucosal interleukin-13 expression to alter tight junction ion selectivity. J Biol Chem. 2010; 285:12037-12046.
21. Blair S A, et al. Epithelial myosin light chain kinase expression and activity are upregulated in inflammatory bowel disease. Lab Invest. 2006; 86:191-201.
22. Utech M, et al. Mechanism of IFN-gamma-induced endocytosis of tight junction proteins: myosin II-dependent vacuolarization of the apical plasma membrane. Mol Biol Cell. 2005; 16:5040-5052.
23. Zolotarevsky Y, et al. A membrane-permeant peptide that inhibits MLC kinase restores barrier function in in vitro models of intestinal disease. Gastroenterology. 2002; 123:163-172.
24. Chowdhury S R, et al. Transcriptome profiling of the small intestinal epithelium in germfree versus conventional piglets. BMC Genomics. 2007; 8:215.
25. Ghoshal U C, et al. The gut microbiota and irritable bowel syndrome: friend or foe? Int J Inflam. 2012; 2012:151085.
26. Sender R, et al. Revised Estimates for the Number of Human and Bacteria Cells in the Body. PLoS Biol. 2016; 14:e1002533.
27. Craven M, et al. Inflammation drives dysbiosis and bacterial invasion in murine models of ileal Crohn's disease. PLoS One. 2012; 7:e41594.
28. Eaves-Pyles T, et al. *Escherichia coli* isolated from a Crohn's disease patient adheres, invades, and induces inflammatory responses in polarized intestinal epithelial cells. Int J Med Microbiol. 2008; 298:397-409.
29. Chassaing B, et al. Intestinal epithelial cell toll-like receptor 5 regulates the intestinal microbiota to prevent low-grade inflammation and metabolic syndrome in mice. Gastroenterology. 2014; 147:1363-1377.

30. Berkes J, et al. Intestinal epithelial responses to enteric pathogens: effects on the tight junction barrier, ion transport, and inflammation. Gut. 2003; 52:439-451.
31. Liao A P, et al. *Salmonella* type III effector AvrA stabilizes cell tight junctions to inhibit inflammation in intestinal epithelial cells. PLoS One. 2008; 3:e2369.
32. Ulluwishewa D, et al. Regulation of tight junction permeability by intestinal bacteria and dietary components. J Nutr. 2011; 141:769-776.
33. Ericsson A C, et al. Segmented filamentous bacteria: commensal microbes with potential effects on research. Comp Med. 2014; 64:90-98.
34. Yin Y, et al. Comparative analysis of the distribution of segmented filamentous bacteria in humans, mice and chickens. ISME J. 2013; 7:615-621.
35. Jepson M A, et al. Actin accumulation at sites of attachment of indigenous apathogenic segmented filamentous bacteria to mouse ileal epithelial cells. Infect Immun. 1993; 61:4001-4004.
36. Meyerholz D K, et al. Segmented filamentous bacteria interact with intraepithelial mononuclear cells. Infect Immun. 2002; 70:3277-3280.
37. Ivanov I I, et al. Induction of intestinal Th17 cells by segmented filamentous bacteria. Cell. 2009; 139:485-498.
38. Panea C, et al. Intestinal Monocyte-Derived Macrophages Control Commensal-Specific Th17 Responses. Cell Rep. 2015; 12:1314-1324.
39. Knights D, et al. Complex host genetics influence the microbiome in inflammatory bowel disease. Genome Med. 2014; 6:107.
40. Lozupone C, Knight R. UniFrac: a new phylogenetic method for comparing microbial communities. Appl Environ Microbiol. 2005; 71:8228-8235.
41. Chassaing B, et al. Crohn disease—associated adherent-invasive *E. coli* bacteria target mouse and human Peyer's patches via long polar fimbriae. J Clin Invest. 2011; 121:966-975.
42. Kitamura Y, et al. Regulation by gut commensal bacteria of carcinoembryonic antigen-related cell adhesion molecule expression in the intestinal epithelium. Genes Cells. 2015; 20:578-589.

What is claimed is:

1. A method of detecting carcinoembryonic antigen-related cell adhesion molecule (CEACAM) protein expression in intestinal epithelial cells from a patient with a loss of function mutation in a protein tyrosine phosphatase non-receptor type 2 (PTPN2) gene, the method comprising:
   contacting the intestinal epithelial cells with an antibody that specifically binds the CEACAM protein, wherein the CEACAM protein is CEACAM1 or CEACAM6, and
   detecting antibod bound to the intestinal epithelial cells.
2. The method of claim 1, wherein the CEACAM protein is CEACAM6.
3. The method of claim 1, wherein the antibody is labeled.
4. The method of claim 1, wherein the biological sample is an ileal biopsy.
5. The method of claim 1, wherein the CEACAM protein is CEACAM6 and the biological sample is an ileal biopsy.

* * * * *